(12) United States Patent
Argentine

(10) Patent No.: US 8,915,933 B2
(45) Date of Patent: Dec. 23, 2014

(54) SUTURING DEVICE HAVING A RETRACTABLE DISTAL TIP AND METHOD FOR SEALING AN OPENING IN A BLOOD VESSEL OR OTHER BIOLOGICAL STRUCTURE

(71) Applicant: Medtronic Vascular, Inc., Santa Rosa, CA (US)

(72) Inventor: Jeffery Argentine, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 302 days.

(21) Appl. No.: 13/667,143

(22) Filed: Nov. 2, 2012

(65) Prior Publication Data

US 2014/0128887 A1    May 8, 2014

(51) Int. Cl.
*A61B 17/04* (2006.01)

(52) U.S. Cl.
USPC ........................................................ 606/144

(58) Field of Classification Search
USPC .................. 606/144, 145, 146, 148, 149, 150
See application file for complete search history.

(56) References Cited

U.S. PATENT DOCUMENTS

| | | |
|---|---|---|
| 5,304,184 A | 4/1994 | Hathaway et al. |
| 5,417,699 A | 5/1995 | Klein et al. |
| 5,476,469 A | 12/1995 | Hathaway et al. |
| 5,527,322 A | 6/1996 | Klein et al. |
| 5,613,974 A | 3/1997 | Andreas et al. |
| 5,720,757 A | 2/1998 | Hathaway et al. |
| 5,779,719 A | 7/1998 | Klein et al. |
| 5,792,152 A | 8/1998 | Klein et al. |
| 5,797,929 A | 8/1998 | Andreas et al. |
| 5,810,850 A | 9/1998 | Hathaway et al. |
| 5,820,631 A | 10/1998 | Nobles |
| 5,860,990 A | 1/1999 | Nobles et al. |
| 5,860,991 A | 1/1999 | Klein et al. |
| 5,902,311 A | 5/1999 | Andreas et al. |
| 5,921,994 A | 7/1999 | Andreas et al. |
| 6,036,699 A | 3/2000 | Andreas et al. |
| 6,117,144 A | 9/2000 | Nobles et al. |
| 6,117,145 A | 9/2000 | Wood et al. |
| 6,132,440 A | 10/2000 | Hathaway et al. |
| 6,136,010 A | 10/2000 | Modesitt et al. |
| 6,171,317 B1 | 1/2001 | Jackson et al. |

(Continued)

FOREIGN PATENT DOCUMENTS

| | | |
|---|---|---|
| EP | 0941698 | 5/2005 |
| EP | 1570790 | 11/2008 |
| WO | WO00/69342 | 5/2002 |

OTHER PUBLICATIONS

U.S. Appl. No. 12/463,046, filed May 8, 2009, Nobles et al.

*Primary Examiner* — Jonathan W Miles

(57) ABSTRACT

A suturing device including an elongated body, a distal tip, at least two support arms, and at least two extendable and retractable needles. The distal tip is moveable between an extended position in which the distal tip distally extends from a distal end of the elongated body and a retracted position in which the distal tip is disposed within the elongated body. The support arms are pivotally coupled to the distal tip. When the distal tip is in the extended position, each support arm is in a collapsed position disposed within the elongated body, and when the distal tip is in the retracted position, each support arm is in a deployed position extending radially away from the elongated body. Each needle includes a distal end configured to penetrate through a vessel wall and capture a suture releasably held within a portion of a support arm.

20 Claims, 10 Drawing Sheets

(56) References Cited

U.S. PATENT DOCUMENTS

| | | |
|---|---|---|
| 6,206,893 B1 | 3/2001 | Klein et al. |
| 6,245,079 B1 | 6/2001 | Nobles et al. |
| 6,348,059 B1 | 2/2002 | Hathaway et al. |
| 6,355,050 B1 | 3/2002 | Andreas et al. |
| 6,517,553 B2 | 2/2003 | Klein et al. |
| 6,551,331 B2 | 4/2003 | Nobles et al. |
| 6,558,399 B1 | 5/2003 | Isbell et al. |
| 6,562,052 B2 | 5/2003 | Nobles et al. |
| 6,730,102 B1 | 5/2004 | Burdulis, Jr. et al. |
| 6,733,509 B2 | 5/2004 | Nobles et al. |
| 6,746,457 B2 | 6/2004 | Dana et al. |
| 6,749,615 B2 | 6/2004 | Burdulis et al. |
| 6,911,034 B2 | 6/2005 | Nobles et al. |
| 6,964,668 B2 | 11/2005 | Modesitt et al. |
| 7,001,400 B1 | 2/2006 | Modesitt et al. |
| 7,004,952 B2 | 2/2006 | Nobles et al. |
| 7,029,480 B2 | 4/2006 | Klein et al. |
| 7,029,481 B1 | 4/2006 | Burdulis, Jr. et al. |
| 7,060,078 B2 | 6/2006 | Hathaway et al. |
| 7,090,686 B2 | 8/2006 | Nobles et al. |
| 7,094,246 B2 | 8/2006 | Anderson et al. |
| 7,108,710 B2 | 9/2006 | Anderson |
| 7,147,646 B2 | 12/2006 | Dana et al. |
| 7,235,087 B2 | 6/2007 | Modesitt et al. |
| 7,377,927 B2 | 5/2008 | Burdulis, Jr. et al. |
| 7,390,328 B2 | 6/2008 | Modesitt |
| 7,416,556 B2 | 8/2008 | Jackson |
| 7,445,626 B2 | 11/2008 | Songer et al. |
| 7,449,024 B2 | 11/2008 | Stafford |
| 7,462,188 B2 | 12/2008 | McIntosh |
| 7,601,161 B1 | 10/2009 | Nobles et al. |
| 2003/0120287 A1 | 6/2003 | Gross et al. |
| 2003/0181926 A1 | 9/2003 | Dana et al. |
| 2003/0216755 A1 | 11/2003 | Shikhman et al. |
| 2004/0097968 A1 | 5/2004 | Shikhman et al. |
| 2004/0210238 A1 | 10/2004 | Nobles et al. |
| 2005/0143762 A1 | 6/2005 | Paraschac et al. |
| 2005/0228407 A1 | 10/2005 | Nobles et al. |
| 2005/0251203 A1 | 11/2005 | Shikhman |
| 2006/0069397 A1 | 3/2006 | Nobles et al. |
| 2006/0195120 A1 | 8/2006 | Nobles et al. |
| 2006/0259047 A1 | 11/2006 | Hathaway et al. |
| 2006/0264977 A1 | 11/2006 | Dana et al. |
| 2006/0265010 A1 | 11/2006 | Paraschac et al. |
| 2006/0265012 A1 | 11/2006 | Anderson |
| 2006/0282102 A1 | 12/2006 | Nobles et al. |
| 2006/0287673 A1 | 12/2006 | Brett et al. |
| 2006/0293700 A1 | 12/2006 | Dana et al. |
| 2007/0010829 A1 | 1/2007 | Nobles et al. |
| 2007/0032798 A1 | 2/2007 | Pantages et al. |
| 2007/0032799 A1 | 2/2007 | Pantages et al. |
| 2007/0043385 A1 | 2/2007 | Nobles et al. |
| 2007/0135823 A1 | 6/2007 | Hathaway et al. |
| 2007/0167959 A1 | 7/2007 | Modesitt et al. |
| 2007/0276410 A1 | 11/2007 | McIntosh |
| 2007/0276413 A1 | 11/2007 | Nobles |
| 2007/0276414 A1 | 11/2007 | Nobles |
| 2007/0282354 A1 | 12/2007 | McIntosh |
| 2008/0004640 A1 | 1/2008 | Ellingwood |
| 2008/0045979 A1 | 2/2008 | Ma |
| 2008/0058839 A1 | 3/2008 | Nobles et al. |
| 2008/0249545 A1 | 10/2008 | Shikhman |
| 2008/0269786 A1 | 10/2008 | Nobles et al. |
| 2008/0287967 A1 | 11/2008 | Andreas et al. |
| 2008/0319458 A1 | 12/2008 | Reynolds |
| 2009/0005793 A1 | 1/2009 | Pantages et al. |
| 2009/0018574 A1 | 1/2009 | Martin |
| 2009/0036906 A1 | 2/2009 | Stafford |
| 2009/0048615 A1 | 2/2009 | McIntosh |
| 2009/0088779 A1 | 4/2009 | Zung et al. |
| 2009/0099578 A1 | 4/2009 | Heneveld et al. |
| 2009/0157100 A1 | 6/2009 | Voss |
| 2009/0157101 A1 | 6/2009 | Reyes et al. |
| 2009/0157105 A1 | 6/2009 | Zung et al. |

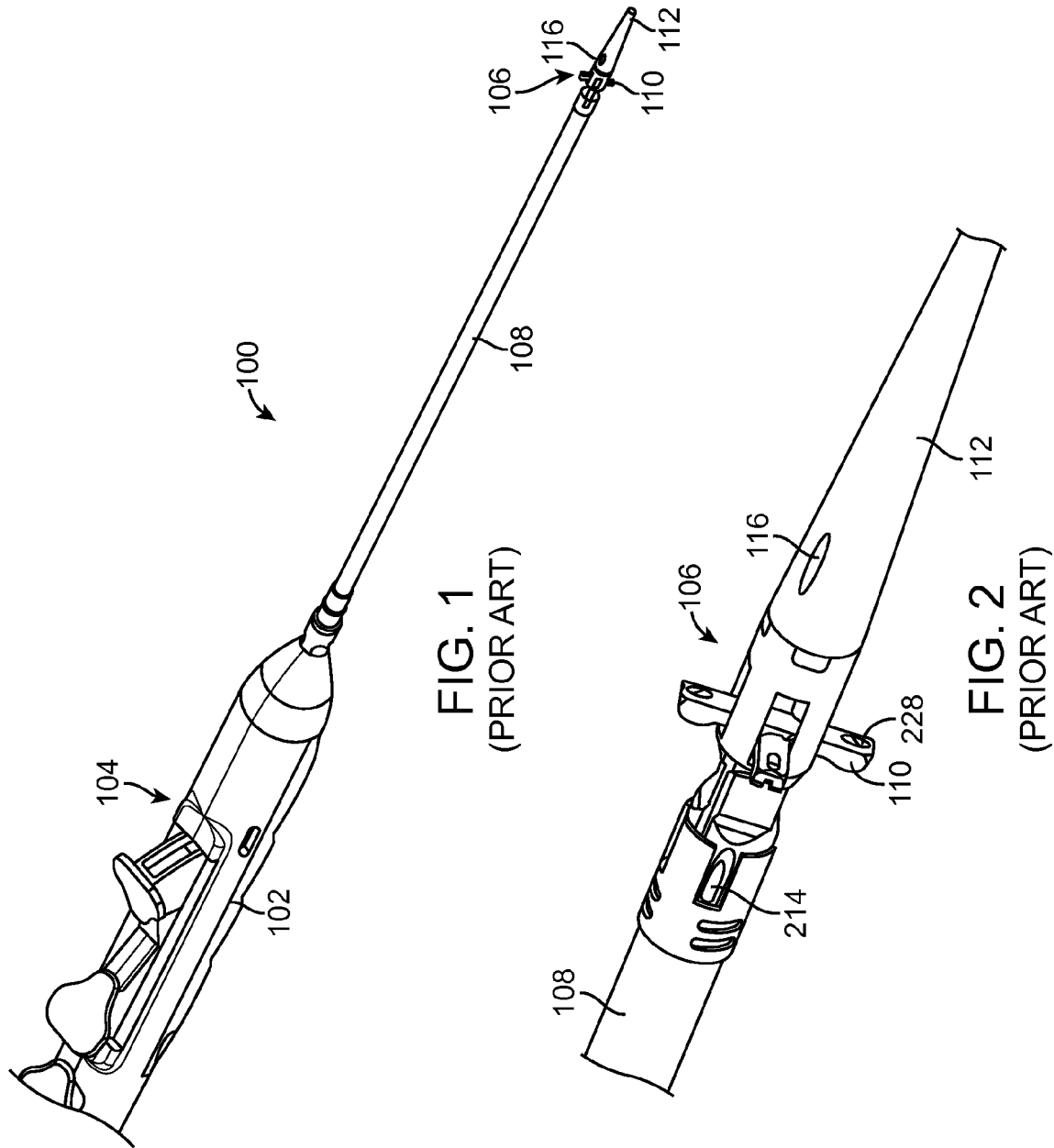

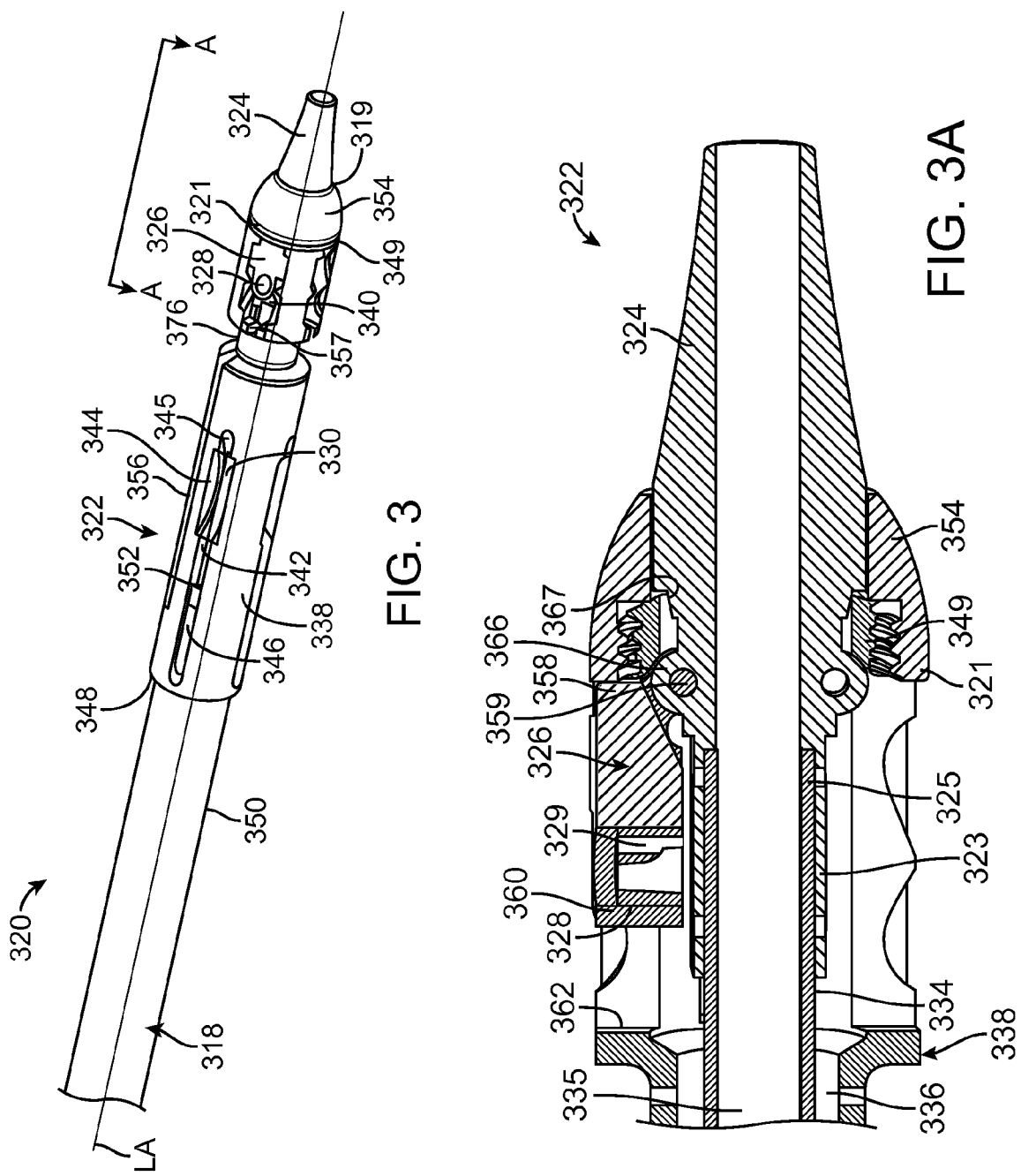

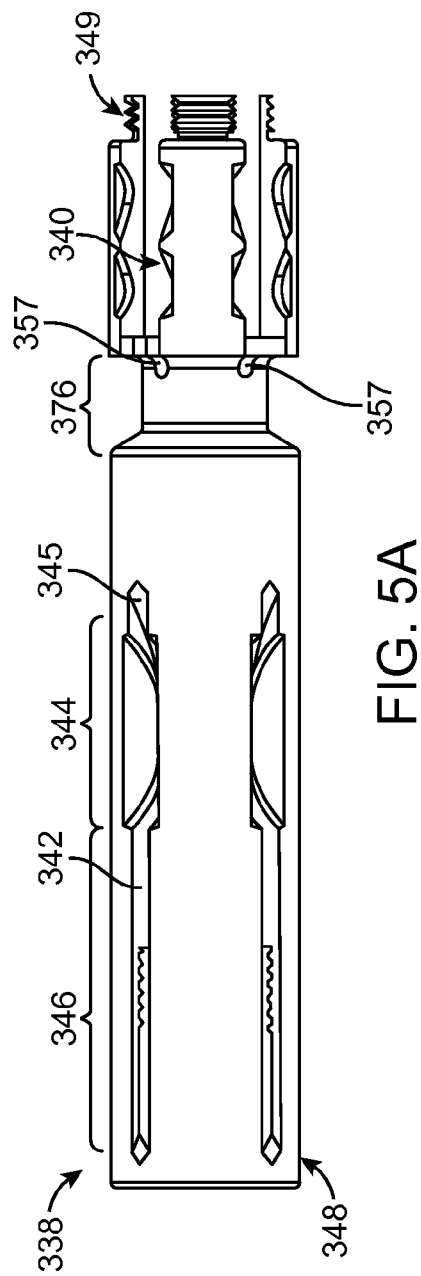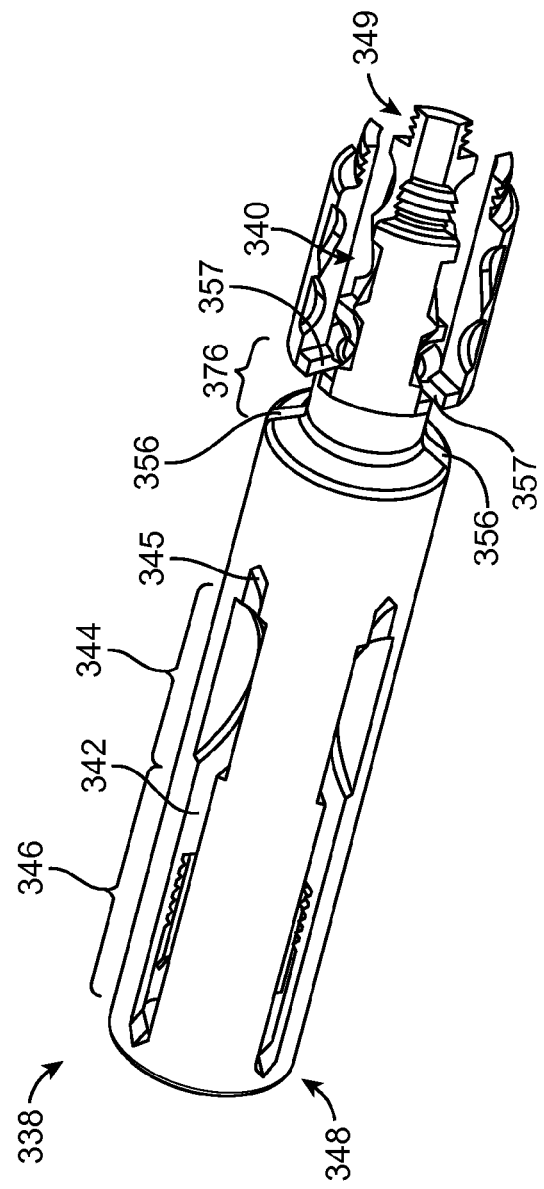

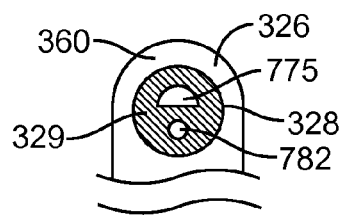
FIG. 7
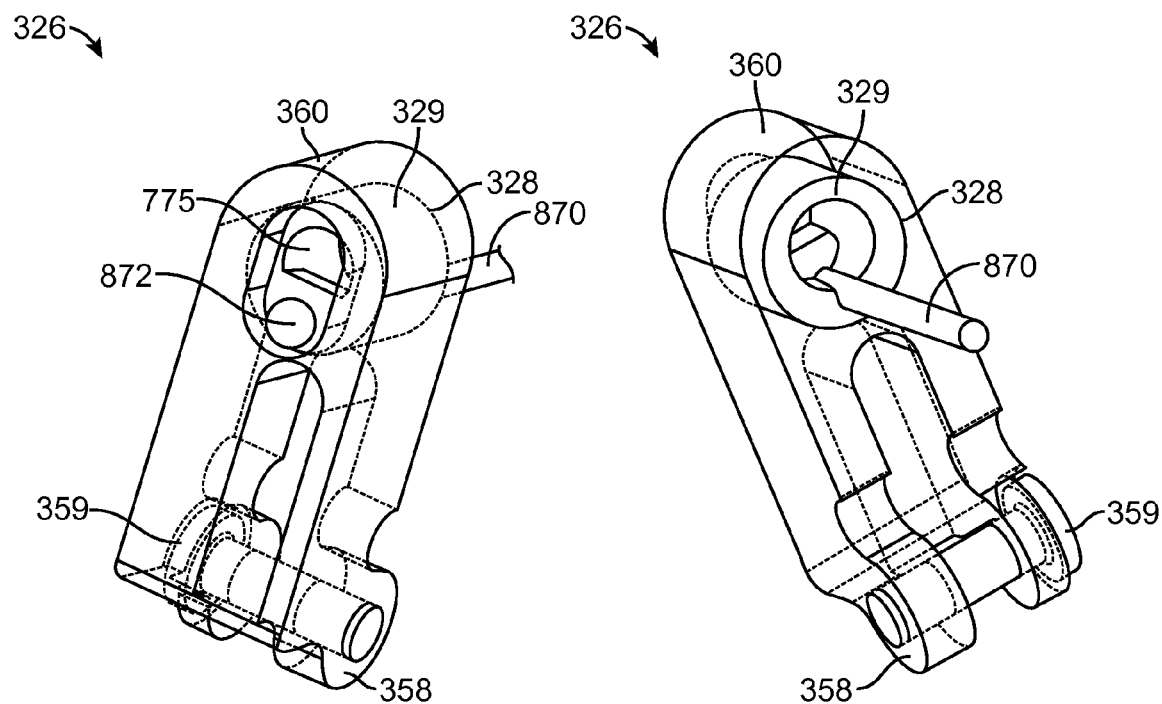
FIG. 8A
FIG. 8B

SUTURING DEVICE HAVING A RETRACTABLE DISTAL TIP AND METHOD FOR SEALING AN OPENING IN A BLOOD VESSEL OR OTHER BIOLOGICAL STRUCTURE

FIELD OF THE INVENTION

Embodiments hereof relate to medical suturing devices. More particularly, embodiments hereof relate to suturing devices for closing an opening in an arterial or other biological tissue wall that is not directly accessible to the physician.

BACKGROUND OF THE INVENTION

Various cardiovascular procedures, such as angioplasty, stent placement and atherectomy, require gaining access to the vasculature. Access to the vasculature typically is through the femoral artery and is percutaneous, involving insertion of a needle in the region of the groin to form a track through subcutaneous tissue and to puncture and create an arteriotomy in the femoral artery. A guidewire is then advanced through the needle and into the femoral artery. The needle then is removed. An introducer sheath, which is typically a single lumen catheter with a hemostasis valve on its proximal end, is then advanced over the guidewire, along the track and into the femoral artery. The sheath provides access into the femoral artery, through the arteriotomy, for longer guidewires, catheters or other instrumentalities in order to perform the selected procedure. The hemostasis valve on the introducer sheath is used to prevent extraneous bleed back or to introduce medication into the patient's body.

After the procedure has been completed, the interventional devices are removed and the arteriotomy must be closed. The size of the puncture opening in the artery corresponds to the size of the catheter or percutaneous introducer sheath used, and such devices may typically range in diameter from 5 French for a diagnostic procedure to 6-20 French for a therapeutic procedure. A number of techniques are known to facilitate closure and healing of the arteriotomy. One technique includes application of pressure at the puncture site for a relatively extended length of time. More particularly, compression has traditionally been applied to the puncture site for at least 30-45 minutes for the wound to close naturally after removal of the catheter. Patients are required to remain lying down, essentially motionless and often with a heavy sandbag placed on their upper leg, for several hours to ensure that the bleeding has stopped. The recovery time from the medical procedure may be as little as half of an hour, but the recovery time from the wound can exceed twenty-four hours. Longer recovery times may result in increased expenses, increased patient discomfort, and greater the risk of complications. Other approaches to arteriotomy closure include a compression clamp device, a thrombotic or collagen plug, biological adhesives adapted to seal the arteriotomy, and/or stapling devices.

In addition, medical suturing systems have been proposed to facilitate closure and healing of the arteriotomy and resolve some of the concerns associated with arteriotomy closure after vascular catheterization procedures. FIGS. 1-2 illustrate an exemplary suturing device 100 for suturing arterial vessel walls and other biological tissue. Suturing device 100 is the commercially available SuperStitch™ closure device by Sutura, Inc. of Fountain Valley, Calif. As explained in U.S. Pat. No. 6,117,144 to Nobles et al., herein incorporated by reference in its entirety, suturing device 100 includes extendable/retractable support arms 110, shown in an expanded or deployed configuration in FIGS. 1-2, that are used to hold a suture (not shown in FIGS. 1-2) beyond an outer circumference of a tubular body of the suturing device (and thus beyond the boundaries of the incision/arteriotomy), and extendable/retractable needles 214 (see FIG. 2) that are used to capture the held suture outside the outer circumference. More particularly, suturing device 100 includes a proximal portion 104 having a handle 102 and a distal portion 106 having a tapered distal tip or nosecone 112. An elongated tubular body 108 extends between handle 102 and distal tip 112. Opposing ends of a suture exit from elongated body 108 via a hole or opening 116 formed within distal tip 112 and are removably or temporarily held within openings 228 of support arms 110 (shown in FIG. 2).

In operation, tapered distal tip 112 is advanced through the target arteriotomy and suture arms 110 may be expanded or deployed within the vessel lumen, such that openings 228 of support arms 110 holding the ends of the suture are positioned adjacent to tissue on opposing sides of the arteriotomy. Needles 214 are then distally extended or deployed from corresponding grooves within elongated body 108, piercing and passing through biological tissue to be sutured on opposing sides of the arteriotomy until the distal ends of needles 214 engage the opposing ends of a suture, held within deployed support arms 110. Once the suture ends are captured by needles 214, the needles and captured suture ends are proximally retracted back into elongated body 108. The support arms are collapsed and the device is removed, with the suture ends still captured therein, thereby releasing a segment of the suture within the vessel lumen adjacent to the arteriotomy. The suture ends are pulled and then tied or knotted in order to close the arteriotomy. Handle 102 allows the physician to externally operate support arms 110 and needles 214 inside a blood vessel. In the embodiment depicted, handle 102 has three buttons to actuate three actions: a first action in which support arms 110 are radially deployed to a fully outward position; a second action to distally advance needles 214 and then proximally retract the needles; and a third action in which support arms 110 are returned to a non-deployed state. Embodiments hereof relate to improvements of the suturing device illustrated in FIGS. 1-2.

BRIEF SUMMARY OF THE INVENTION

Embodiments hereof relate to a suturing device, including an elongated body, a distal tip, at least two support arms, and at least two needles. The distal tip is moveable between an extended position in which the distal tip distally extends from a distal end of the elongated body and a retracted position in which the distal tip is disposed within the elongated body. The at least two support arms are pivotally coupled to the distal tip to be actuated by longitudinal movement of the distal tip. Each support arm is in a collapsed position disposed within the elongated body when the distal tip is in the longitudinally or distally extended position and each support arm is in a deployed position extending radially away from the elongated body when the distal tip is in the retracted position. The at least two needle are extendable and retractable relative to the elongated body, and each needle includes a distal end configured to penetrate through a vessel wall and capture a suture releasably held within a portion of a support arm.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a perspective view of an exemplary prior art suturing device for suturing arterial vessel walls and other biological tissue.

FIG. 2 is an enlarged view of a distal portion of the suturing device of FIG. 1.

FIG. 3 is a perspective view of a distal portion of a suturing device according to an embodiment hereof, wherein support arms of the suturing device are collapsed and a distal tip of the suturing device is longitudinally or distally extended.

FIG. 3A is a cross-sectional view taken along line A-A of FIG. 3.

FIGS. 5A and 5B are side and perspective views, respectively, of a needle guide of the suturing device of FIG. 3, wherein the needle guide is shown removed from the suturing device for illustration purposes only.

FIG. 7 is an enlarged end view of a support arm of the suturing device of FIG. 3.

FIGS. 8A and 8B are perspective views of a support arm of the suturing device of FIG. 3, wherein an end of a suture is coupled thereto for illustrative purposes.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as arteries, the invention may also be used in any other body passageways where it is deemed useful. For example, the device could be used to suture other tissue such as a patent ductus arteriosus, a patent foramen ovale, a heart defect, a puncture wound, and the like. Furthermore, there is no intention to be bound by any expressed or implied theory presented in the preceding technical field, background, brief summary or the following detailed description.

Figure 4:
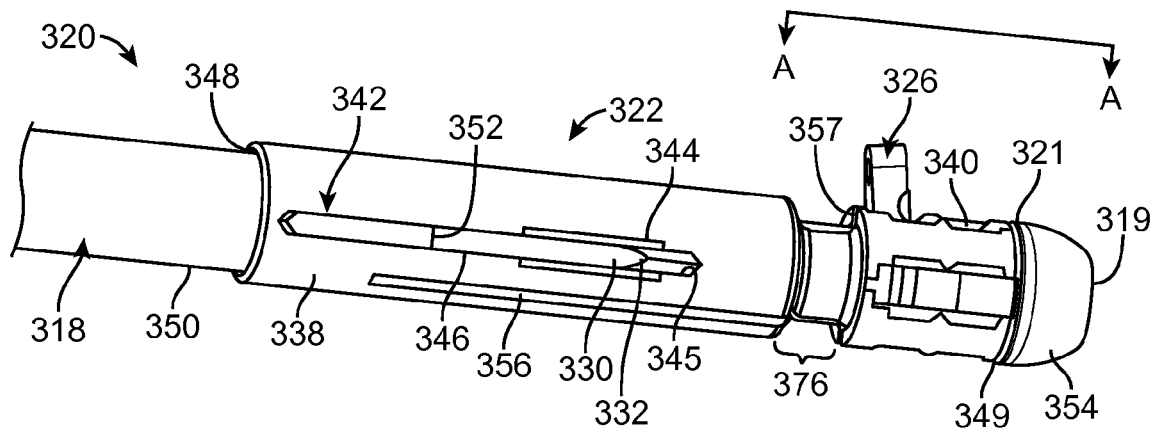
FIG. 4 is a perspective view of the distal portion of the suturing device of FIG. 3, wherein support arms of the suturing device are deployed and a distal tip of the suturing device is retracted.

Referring to FIGS. 3 through 4, a suturing device 320 for suturing arterial vessel walls and other biological tissue is shown. The suturing device may be used to seal a blood vessel following an interventional catheterization procedure. Only a distal portion 322 of suturing device 320 is shown, but it will be understood by one of ordinary skill in the art that a proximal portion of the suturing device includes a handle similar to handle 102 shown in FIG. 1. Suturing device 320 includes an elongated body 318 extending from the handle (not shown) to a retractable tapered distal tip or nosecone 324. Distal tip 324 is longitudinally slidable relative to elongated body between a distally extended position, shown in FIG. 3, in which distal tip 324 distally extends from a distal end 319 of elongated body 318 and a retracted position, shown in FIG. 4, in which the distal tip is disposed within the elongated body. By including a retractable distal tip, suturing device 320 may be utilized for suturing vessel walls of vessels having relatively smaller diameters because the distal tip is retracted during the suturing process, and thereby does not protrude into the vessel and will not interfere with the opposing side of the vessel wall. Since distal tip 324 does not extend beyond distal end 319 of elongated body 318 during the suturing process, device 320 reduces the likelihood that any portion of the device will contact and damage the inner vessel wall opposite the incision/arteriotomy.

Figure 4A:
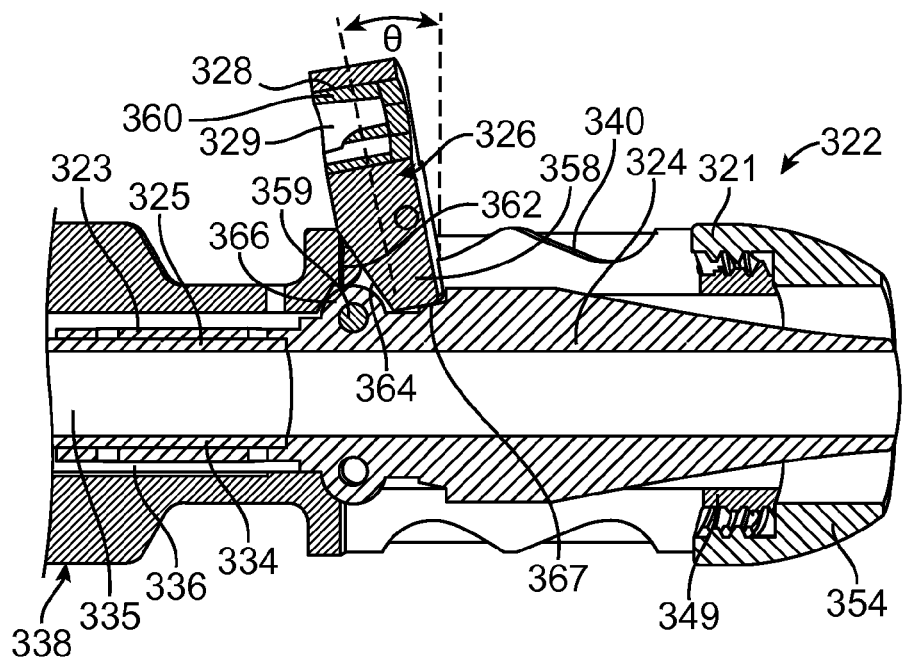
FIG. 4A is a cross-sectional view taken along line A-A of FIG. 4.

FIG. 3A is a cross-sectional view taken along line A-A of FIG. 3, while FIG. 4A is a cross-sectional view taken along line A-A of FIG. 4. The components of suturing device 320 will now be described with reference to FIGS. 3, 3A, 4, and 4A. Elongated body 318 includes an outer shaft 350, an end cap 354, and a needle guide 338 extending between a distal end 352 of outer shaft 350 and a proximal end portion 321 of end cap 354. A distal end of end cap 354 defines distal end 319 of elongated body 318. Each of the outer shaft, the end cap, and the needle guide are hollow tubular components and collectively define at least one continuous lumen 336 through elongated body 318 for housing an inner shaft or rod 334 (see FIG. 3A), which slidingly extends within lumen 336. A proximal end portion 323 of nosecone or distal tip 324 is coupled to a distal end portion 325 of inner shaft 334, and accordingly, movement of inner shaft 334 results in movement of the distal tip. Inner shaft 334 and distal tip 324 may define a continuous lumen 335 for tracking suturing device 320 over a guidewire (not shown).

In addition to defining a portion of lumen 336, outer shaft 350 may define or include a plurality of additional lumens (not shown). For example, at least two needles 330 are slidingly disposed within outer shaft 350 and outer shaft 350 may define individual lumens for housing each needle 330. As will be explained in more detail herein, each needle 330 is a generally straight rod or shaft component which extends the length of outer shaft 350, and has a proximal end extending from the handle of suturing device 320 and a distal end 332 configured to penetrate through the vessel wall and capture a suture end (not shown in FIGS. 3, 3A, 4, and 4A). In addition, outer shaft 350 may include a lumen for housing the length of a suture to prevent the suture from becoming tangled. Another lumen may be included for "bleed back," which lets the physician determine whether distal end 319 of the suturing device remains positioned in the blood vessel/artery during the suturing procedure. Bleed back is accomplished through a lumen defined by distal tip 324, and any other openings in the suturing device. If distal end 319 of the suturing device is still in the blood vessel/artery, the blood pressure measured by the blood coming up into the lumen defined by distal tip 324 will be much greater than if distal end 319 of the suturing device is not in the blood vessel/artery.

Needle guide 338, extending between outer shaft 350 and end cap 354, is a single component or piece having a proximal end 348 which is coupled to distal end 352 of outer shaft 350 via a threaded connection and a distal end 349 which is coupled to proximal end portion 321 of end cap 354 via a threaded connection. As used herein, "threaded connection" includes connection between a first component having female or internal threads and a second component having male or external threads that interlock with the female or internal threads of the first component. Once the first and second components are coupled together via the threaded connection, the components are locked together and move as a unitary structure. As would be understood by one of ordinary skill in the art, needle guide 338 may be connected to outer shaft 350 and end cap 354 by other means, such as adhesives or other mechanical connectors, or may be unitary with one or more of the outer shaft and the end cap. A side view and a perspective view of needle guide 338 removed from suturing device 320 is shown in FIGS. 5A and 5B, respectively, for illustrative purposes only.

Needle guide 338 includes at least two transverse openings or ports 342 that each allow passage of a needle 330 through the needle guide so that the needles may alternate between a retracted position in which each needle is disposed within the elongated body and an extended position in which each needle extends distally and radially outward from a longitudinal axis $L_A$ of elongated body. Needles 330 are extended or deployed in order to penetrate through the vessel wall and capture suture mounting portions and suture ends, as will be explained in more detail herein. As will be understood by one of ordinary skill in the art, the number of ports 342 formed on needle guide 338 corresponds to the number of needles 330 located within the elongated body of suturing device 320. In an embodiment, each transverse port 342 is a slot or opening which guides a corresponding needle 330 along a particular path. Each transverse port 342 includes a first or proximal segment 346, having a first width only slightly greater than the diameter of a needle 330, and a second or distal segment 344 having a greater width than first segment 346. Distal segment 344 of port 342 has a width greater than proximal segment 346 of port 342 to smoothly allow for full retraction of a needle 330 having a captured suture mounting portion and suture end thereon, as will be explained in more detail herein, while proximal segment 346 permits gradual bending of needle 330. In an embodiment, proximal segment 346 of port 342 is formed via a sawcut and distal segment 344 of port 342 is formed as a milled pocket. When each needle 330 is distally advanced, its distal end 332 (shown in FIG. 4) comes into contact with a curved deflection surface or edge 345 formed within transverse port 342 that operates to guide distal end 332 of needle 330 out of elongated body 318 and causes needle 330 to bend radially outward at an acute angle relative to the longitudinal axis $L_A$ of elongated body 318. As distal end 332 exits from elongated portion 342, each needle gradually bends via proximal segment 346 and assumes the extended position in which each needle extends distally and outwardly from elongated body 318. The angle of the needle deflection ranges between 5 and 25 degrees, and in one embodiment is approximately 19 degrees.

Proximal segment 346 of port 342 allows for gradual or shallow bending of a corresponding needle 330, which reduces the amount of force/energy required to extend the needle and also allows the needle to be formed from stainless steel for improved pushability. In another embodiment, needles 330 may be formed from a material with shape memory such as Nitinol. In an embodiment, the diameter of the needles is approximately 0.019 inches, but needles with other diameters may be used herewith. After needles 330 capture the ends of a suture, needles 330 are proximally refracted back into distal segments 344 of transverse ports 342 and resume their retracted position in which each needle is disposed within the elongated body. When needles 330 are retracted back into elongated body 318, they return to their original generally straight configurations since they are no longer in contact with deflection surface 345 of needle guide 338 that caused the needles to bend radially outward in the extended position.

Needle guide 338 also includes at least two profiled passageways or cams 340 for guiding at least two support arms 326 between a first collapsed position in which each support arm 326 is disposed within and is substantially parallel to elongated body 318, as shown in FIGS. 3 and 3A, and a second deployed position in which each support arm 326 extends radially outwardly away from the elongated body, as shown in FIGS. 4 and 4A. As will be understood by one of ordinary skill in the art, the number of support arms and corresponding passageways 340 also corresponds to the number of needles 330 positioned within the elongated body of suturing device 320. If two needles and two support arms are included on suturing device 320, the support arms are preferably circumferentially spaced at 180 degrees from each other. Similarly, if four support arms are included on suturing device 320, the support arms are preferably circumferentially spaced at 90 degrees from each other. It will be understood by one of ordinary skill in the art that two support arms and two needles are utilized for positioning one suture at an incision/arteriotomy, while four support arms and four needles are utilized for positioning two sutures at an incision/arteriotomy. Each suture has two ends which are held by a pair of support arms and subsequently captured by a pair of needles. Thus, the numbers of needles and support arms can be incorporated into the device to accomplish the specific needs of the application. In the embodiment of FIGS. 3, 3A, 4, and 4A, although not all visible in the side and perspective views, suturing device 320 includes four needles and four support arms and thus would be utilized for positioning two sutures at an incision/arteriotomy. However, for sake of clarity and illustration, only one support arm is shown in order to display the passageways 340 on needle guide 338 as well.

Figure 6A:
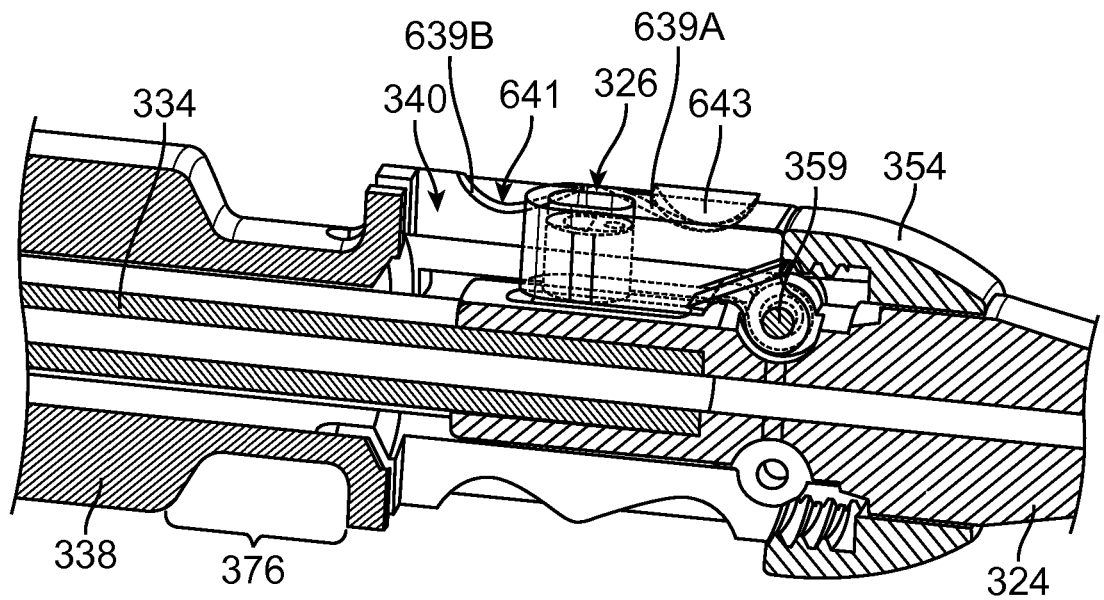
FIG. 6A is a sectional view of the distal portion of the suturing device of FIG. 3, wherein support arms of the suturing device are collapsed and shown in phantom.
Figure 6B:
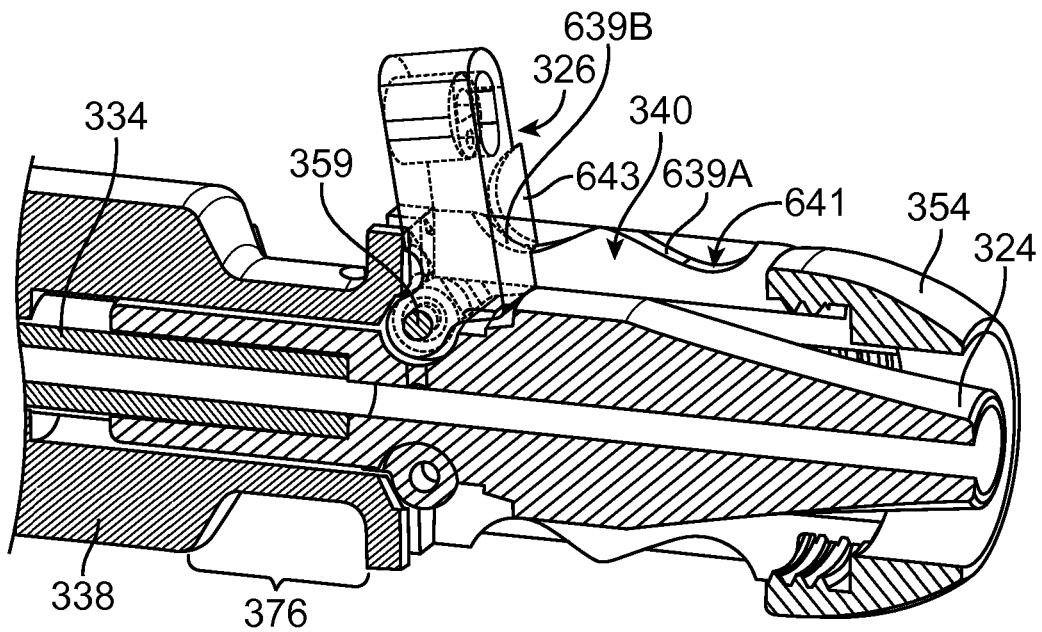
FIG. 6B is a sectional view of the distal portion of the suturing device of FIG. 3, wherein support arms of the suturing device are deployed and shown in phantom.

When support arm 326 is in the first collapsed position, distal tip 324 is in its extended position and suture mounting portion 329 is releasably held within passageway 340 of needle guide 338 as shown in FIG. 3A. A first end 358 of each support arm 326 is pivotally coupled via a hinge or rotatable joint 359 to distal tip or nosecone 324 and thus is actuated by movement of the distal tip or nosecone as explained in more detail herein. When inner shaft 334 and distal tip 324 are retracted, distal tip 324 is retracted within elongated body 318 and suture mounting portion 329 of support arm 326 rotates to the second deployed position to radially extend suture mounting portion 329 outwardly away from elongated body 318. With additional reference to the sectional views of FIGS. 6A and 6B, which illustrates support arms 326 in a collapsed position and a deployed positioned, respectively, support arms 326 operate as cam followers in that they follow a profile or contoured outer surface 641 (shown on FIGS. 6A and 6B)

of passageways 340 in order to deploy/move radially outward or collapse/return to lay flat. Each support arm 326 is sized to fit within a corresponding passageway 340, and includes a protrusion 643 on opposing sides thereof for fits within contoured outer surface 641. As inner shaft 334 and distal tip 324 are retracted, support arm 326 is also retracted and pulled back within passageway 340 such that protrusion 643 of support arm 326 rides along contoured outer surface 641. As protrusion 643 of support arm 326 rides along contoured outer surface 641, support arm 326 is radially deployed as protrusion 643 contacts or passes over two curved portions 639A, 639B having of contoured outer surface 641. Via hinge 359, support arm 326 pivots or rotates away from elongate body 318/needle guide 338 as inner shaft 334 and distal tip 324 continue to be retracted.

Support arm 326 is radially deployed until it contacts a deflection surface or edge 362 formed at a proximal end of passageway 340 of needle guide 338. More particularly, pivot or rotation of support arm 326 continues until a protrusion 366 formed on distal tip 324 contacts deflection edge 362 of needle guide 338, whereby support arm 326 is fixed in its deployed or extended position at an angle θ with respect to an axis perpendicular to the longitudinal axis $L_A$ of elongate body 318. A bottom surface or face 364 of support arm 326 is wedged or locked between deflection edge 362 of needle guide 338 and a stepped surface 367 formed on an outer surface of distal tip 324. Stepped surface 367 is positioned adjacent to protrusion 366 on distal tip 324. Since support arm 326 is wedged or locked in a fixed position, it is prevented from pivoting or rotating any further than the configuration shown in FIGS. 4 and 4A. In embodiments hereof, angle θ ranges between 0 and 25 degrees, and in an embodiment, angle θ equals 19 degrees.

With additional reference to FIG. 7 and FIGS. 8A-8B, a second end 360 of each support arm 326 is radially spaced apart from suturing device 320 when support arm 326 is in the second deployed position. Second end 360 of each support arm 326 includes an annular recess or bore 328 with a suture mounting portion 329 releasably or temporarily mounted therein. Referring to FIG. 7, suture mounting portion 329 includes a first opening 775 and a second opening 782 formed therethrough. Suture mounting portion 329 is formed of a soft material such as but not limited to polypropylene. In an embodiment, suture mounting portion 329 is plastic molded into recess 328 of support arm 326 via injection molding. By forming suture mounting portion 329 via injection molding rather than positioning it into recess 328 via press fit, suture mounting portion 329 and openings 775, 782 formed therein do not get deformed during manufacturing. In addition, forming suture mounting portion 329 via injection molding eliminates tight tolerances required when positioning a suture mounting portion into the recess via press fit. Second opening 782 of suture mounting portion 329 is relatively smaller than first opening 775 and is configured to receive a suture 870 therethrough. As shown in FIGS. 8A and 8B, an end 872 of suture 870 is passed through opening 782 and end 872 is formed into a knot having a diameter greater than opening 782, thereby coupling suture 870 to suture mounting portion 329. As explained in more detail herein, first opening 775 is configured to receive distal end 332 of needle 330 such that the distal end of the needle forms a friction or interference fit with suture mounting portion 329.

Figure 9:
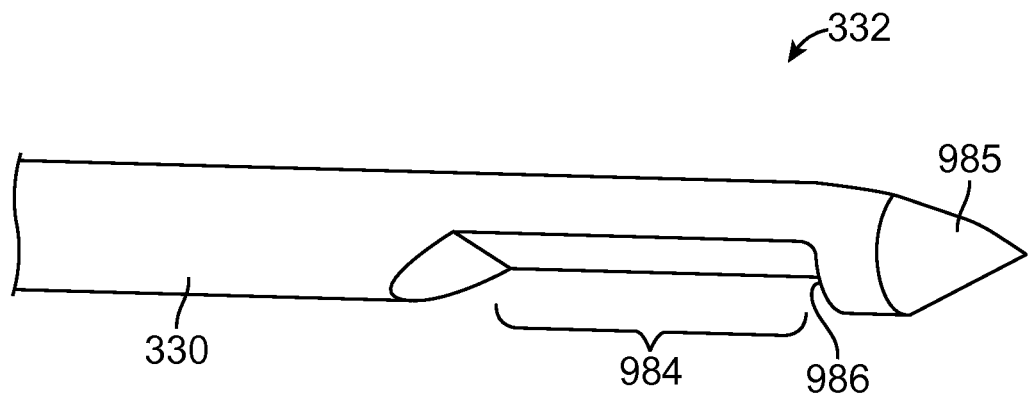
FIG. 9 is a perspective view of a distal portion of a needle of the suturing device of FIG. 3, wherein the needle is shown removed from the suturing device for illustration purposes only.
Figure 10:
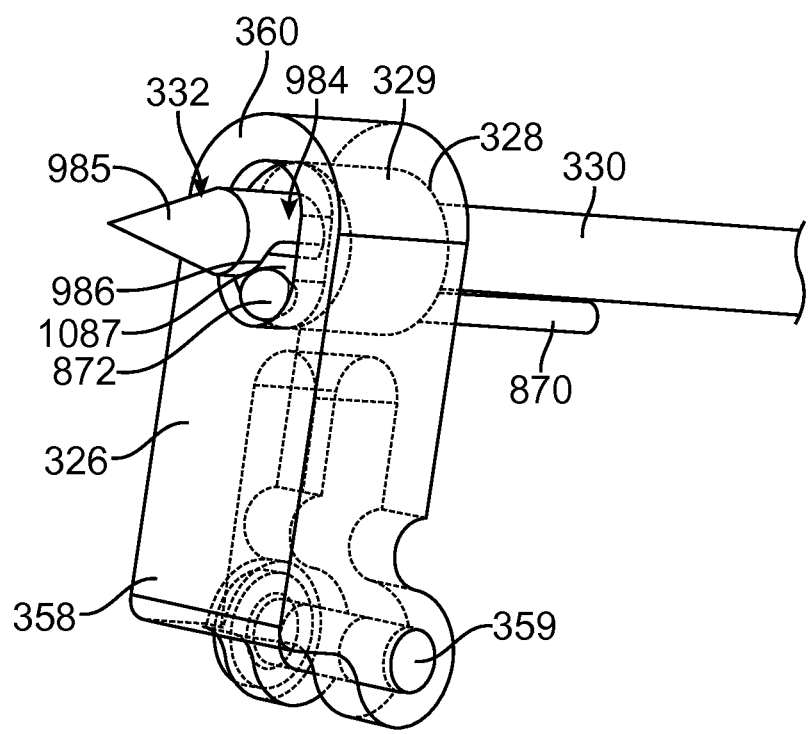
FIG. 10 is a perspective view of a support arm of the suturing device of FIG. 3, wherein an end of a suture and a distal end of a needle is coupled thereto for illustrative purposes.
Figure 11:
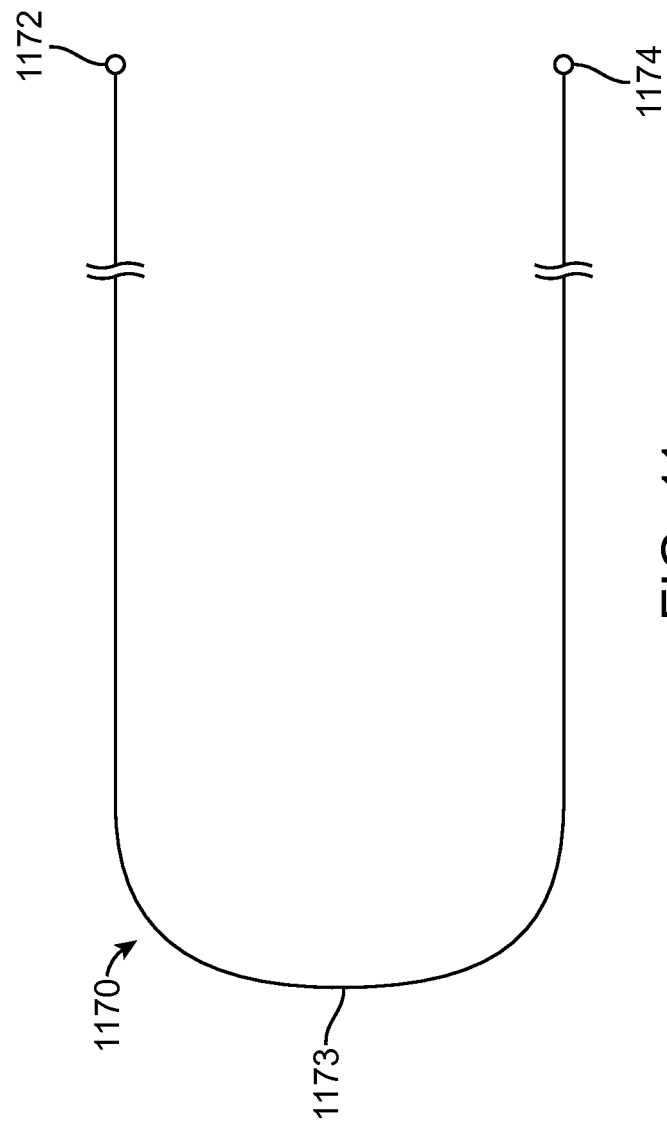
FIG. 11 is a side view of a suture strand to be utilized with suturing devices according to embodiments hereof.

When deployed, support arms 326 hold the ends of a suture against an inside surface of the vessel radial outward of an outer circumference of elongated body 318 and thus radially outward of a boundary of the incision/arteriotomy through which the elongated body has been inserted, and then needles 330 are used to pierce a wall of the vessel, at points that are radially outward of the incision/arteriotomy, to capture the suture mounting portions 329 holding the suture ends. Distal ends 332 of needles 330 are configured to capture suture mounting portions 329 releasably held within recesses 328 of support arms 326. As shown in FIG. 9, each needle 330 includes an integral needle portion 984 having a reduced diameter that forms a stepped edge or surface 986 adjacent to a barbed or pointed distal tip 985. Integral needle portion 984 has a D-shaped cross-section, while the length of needle 330 has a circular cross-section. When distal tip 985 of each needle 330 is inserted into second opening 775 of suture mounting portion 329, as shown in FIG. 10, suture mounting portion 329 plastically deforms to allow passage of needle 330. Once distal tip 985 passes through second opening 775, needle 330 is inserted or distally advanced until integral needle portion 984 of needle 330 having a reduced diameter is centered within second opening 775, with stepped surface 986 abutting against a distal face or surface 1087 of suture mounting portion 329. Once integral needle portion 984 of needle 330 having a reduced diameter is centered within second opening 775, suture mounting portion 329 recovers its original shape and needle 330 is engaged in a geometric relationship with suture mounting portion 329 via stepped surface 986 and distal face or surface 1087 of suture mounting portion 329. Opening 775 of suture mounting portion 329 may be of any appropriate shape to engage needle 330, but in one embodiment, opening 775 is D-shaped and approximately the same size as integral needle portion 984 in order to result in improved engagement/retention of needle 330.

Once distal end 332 of needle 330 engages and is coupled to suture mounting portion 329, needle 330 and suture mounting portion 329 coupled thereto are refracted back into needle guide 338. More particularly, the inner diameter of recess 328 of support arm 326 is approximately equal to, or slightly less than, the outer diameter of suture mounting portion 329. As such, a minimal interference or friction fit holds suture mounting portion 329 within support arm 326. When distal end 332 of needle 330 engages and couples to suture mounting portion 329, the geometric relationship between needle 330 and suture mounting portion 329 is stronger than the interference or friction fit which holds suture mounting portion 329 within support arm 326. As such, when needle 330 is retracted away from support arm 326, suture mounting portion 329 remains coupled to needle 330 and thus is removed or detached from annular recess 328 support arm 326.

Notably, the deployed position of support arms 326 provides a stable base or foundation for holding the suture mounting portions 329 when the distal end of the needles come in contact with support arms 326. With support arm 326 wedged or locked between needle guide 338 and distal tip 324 as described above, support arms 326 cannot open any farther and are in a rigid, locked position to facilitate the proper removal of suture mounting portions 329 (having the suture ends coupled thereto) from recesses 328 of support arms 326.

After the suture ends are captured, prior to removal of suturing device 320, support arms 326 must revert or collapse back into passageway 340 of needle guide 338 to the first collapsed position in which support arms 326 are located within and substantially parallel to elongated body 318. In the first position, support arms 326 are substantially flush with the outer surface of elongated body 318 to reduce the likelihood that the support arms will catch on the vessel walls of the vasculature during insertion and removal of the suturing device. In order to collapse support arms 326 for removal of suturing device 320, inner shaft 334 and distal tip 324 are distally advanced. Operating as a cam follower, support arm 326 is also distally advanced or pushed forward within passageway 340 such that protrusion 643 of support arm 326 rides along or follows contoured outer surface 641 of passageway 340 (which operates as a cam) to collapse/return to the first collapsed position as protrusion 643 contacts or passes over curved portions 639A, 639B of contoured outer surface 641. Thus, when inner shaft 334 and distal tip 324 are distally advanced, support arm 326 collapses back into passageway 340 of needle guide 338.

Needle guide 338 also includes an intermediate neck portion 376 having a reduced outer diameter as compared to the remaining length of the needle guide. As will be explained in more detail herein, intermediate neck portion 376 is utilized when loading a suture within suturing device 320. One or more proximal suture guides or slots 356 proximally extend from a proximal end of intermediate neck portion 376 and two or more distal suture guides or slots 357 distally extend from a distal end of intermediate neck portion 376. In particular, in FIGS. 3 and 4, two opposing proximal suture guides 356 (only one of which is visible in the perspective views of FIGS. 3-4), which are slots or passageways formed through the needle guide, each serve as an exit location for a suture extending within elongate body 318. Since suturing device 320 is utilized for positioning two sutures at an incision/arteriotomy via four needles and four support arms, suturing device 320 includes a proximal suture guide 356 for housing each of the sutures. Similarly, distal suture guides 357 are also slots or passageways formed through the needle guide extending between intermediate neck portion 376 and each passageway 340. Each distal suture guide 357 and each proximal suture guide 356 extends from an inside surface of the needle guide to an outer surface of the needle guide, and may be considered a transverse opening formed through a sidewall of the needle guide. FIGS. 12A-12G describe how a suture is loaded into a suturing device according to an embodiment hereof and the functions of proximal and distal suture guides 356, 357 are described in detail.

Referring now to FIGS. 11 and 12A-12G, the method of utilizing a suturing device according to an embodiment hereof to position a suture 1170 in situ will be described. Suture 1170 is shown laid out flat for illustrative purposes in FIG. 6. Suture 1170 is a continuous strand or filament of material having a first end 1172 and a second end 1174. Suturing device 320, a distal end portion of which is shown in FIGS. 12A-12F, is utilized for positioning an intermediate necked portion or segment 1173 of suture 1170 adjacent to an incision/arteriotomy of a vessel. It will be understood by one of ordinary skill in the art that intermediate portion 1173 of suture 1170 is called out for illustrative purposes only and is not structurally different from the remaining length of suture 1170. Exemplary materials for suture 1170 include but are not limited to a monofilament or plastic suture material, such as polypropylene.

Figure 12A:
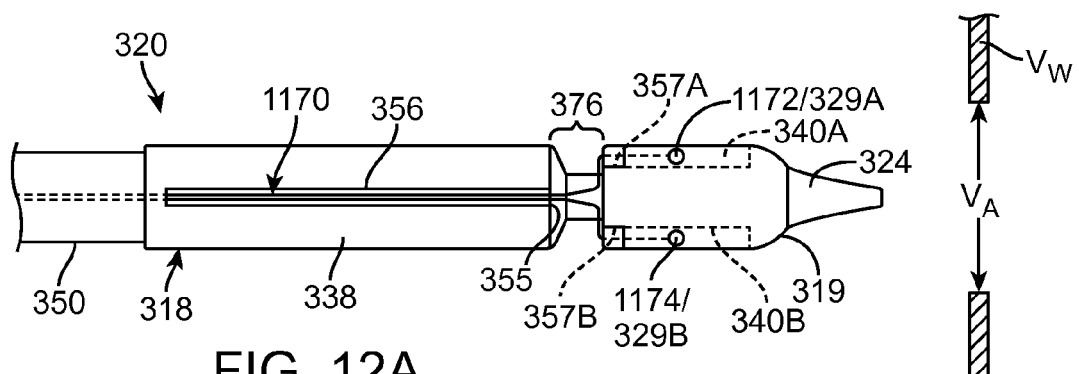
FIGS. 12A-12G illustrate the method of positioning the suture of FIG. 11 in situ with the suturing device of FIG. 3 according to an embodiment hereof.

Referring to FIG. 12A, a side view of a distal end portion of suturing device 320 is shown in a delivery configuration having suture 1170 loaded therein. For sake of simplicity, suturing device 320 is shown in FIGS. 12A-12G illustrate only two needles and two support arms for positioning one suture at an incision/arteriotomy. In the delivery configuration of suturing device 320, distal tip 324 is in the extended position and two support arms 326A, 326B (not shown in FIG. 12A) are in the collapsed position. Suture 1170 is loaded into elongate body 318 of suturing device 320, with first end 1172 of suture 1170 coupled to a suture mounting portion 329A of support arm 326A and second end 1174 of suture 1170 coupled to a suture mounting portion 329B of support arm 326B. A length of suture 1170, including intermediate portion 1173, is positioned within outer shaft 350 of elongate body 318 with two portions of the suture exiting from a distal end 355 of proximal suture guide 356 formed through needle guide 338. When the two portions of suture 1170 exit distal end 355 of proximal suture guide 356, they extend along an outer surface of intermediate neck portion 376 of needle guide 338 having a reduced outer diameter as compared to the remaining length of the needle guide. The two portions of the suture 1170 then diverge from each other, with one portion of suture 1170 extending within distal suture guide 357A (shown in phant12Eom in FIG. 12A) into passageway 340A (shown in phantom in FIG. 12A), which houses support arm 326A. As explained above, first end 1172 of suture 1170 is coupled to a suture mounting portion 329A of support arm 326A. Similarly, the second portion of suture 1170 extends within distal suture guide 357B (shown in phantom in FIG. 12A) into passageway 340B (shown in phantom in FIG. 12A), which houses support arm 326B. Second end 1174 of suture 1170 is coupled to a suture mounting portion 329B of support arm 326B. Thus, distal suture guides 357A, 357B serve as pathways for portions of suture 1170 to be directed into passageways 340A, 340B and support arms 326A, 326B positioned therein.

Notably, when suturing device 320 is in the delivery configuration, no portion of suture 1170 is exposed, i.e., extends beyond the outermost surface of elongate body 318. Suture 1170 is disposed within and/or protected by elongated body 318 along its entire pathway to the support arms, i.e., within outer shaft 350, within proximal suture guide 356 of needle guide 338, alongside reduced diameter portion 376 of needle guide 338, and finally within distal suture guides 357A, 357B and passageways 340A, 340B of needle guide 338. Accordingly, suture 1170 does not extend beyond the outermost surface of elongate body 318 during delivery of suturing device 320 and is therefore protected from damage and/or tangling.

Figure 12B:
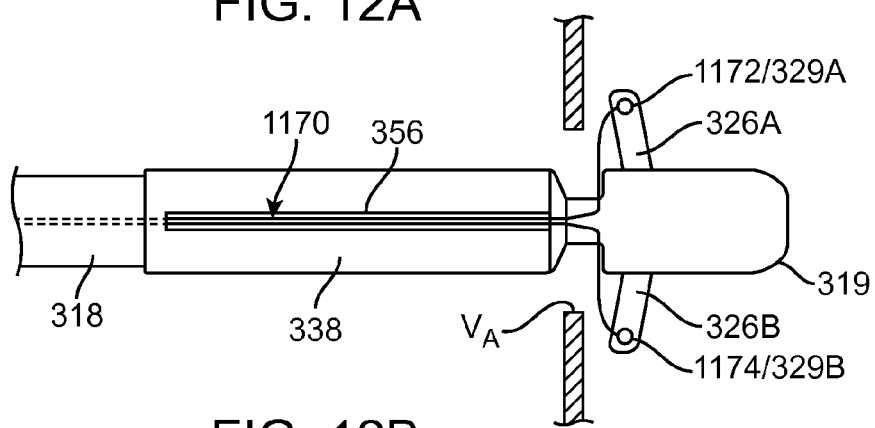

Once distal end 319 of elongate body 318 is positioned through an incision/arteriotomy of a vessel to reside within the lumen of the vessel, radial deployment of support arms 326A, 326B is actuated by longitudinal movement/retraction of distal tip 324 and the inner shaft (not shown in FIGS. 12A-12G) as shown in FIG. 12B and described above with respect to inner shaft 334. First and second ends 1172, 1174 of suture 1170 are still coupled to support arms 326A, 326B, respectively. Support arms 326A, 326B are deployed against the vessel wall $V_W$ on opposing sides of an incision/arteriotomy $V_A$ of a vessel.

Figure 12C:
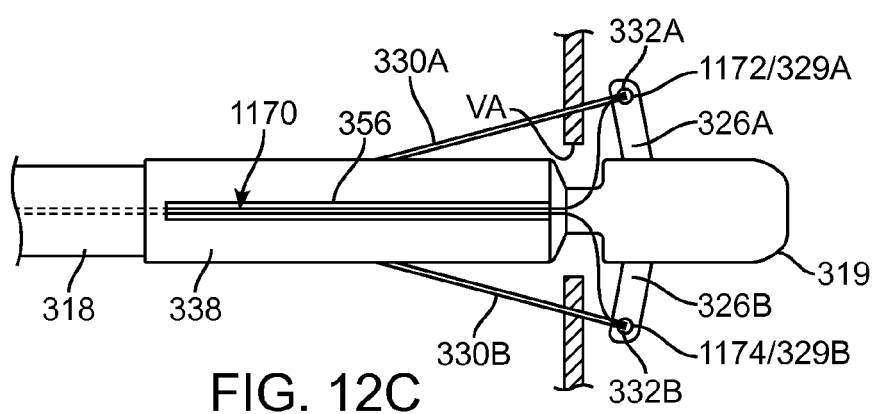

Needles 330A, 330B are then deployed to their extended positions as shown in FIG. 12C and described above. Needles 330A, 330B are radially extended and distally advanced through tissue on opposing sides of the incision/arteriotomy of a vessel until distal ends 332A, 332B engage the suture mounting portions 329A, 329B of support arms 326A, 326B, respectively, which are coupled to first and second ends 1172, 1174 of suture 1170. Accordingly, in situ, needles 330A, 330B create incisions or pathways within tissue on opposing sides of the incision/arteriotomy.

Figure 12D:
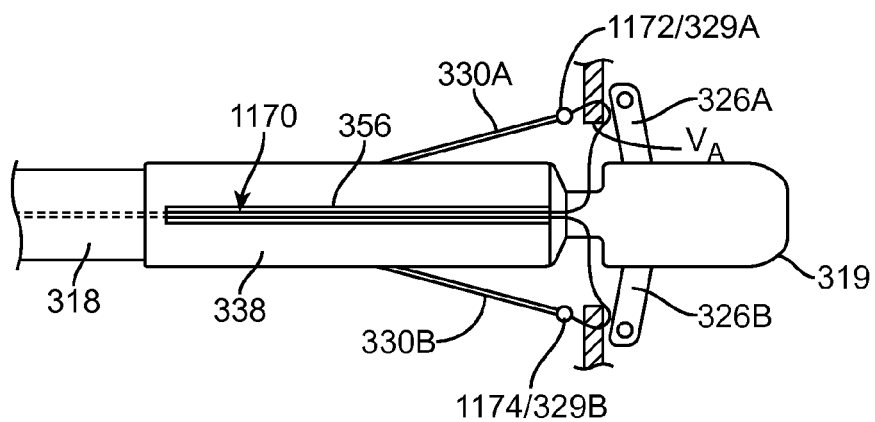
Figure 12E:
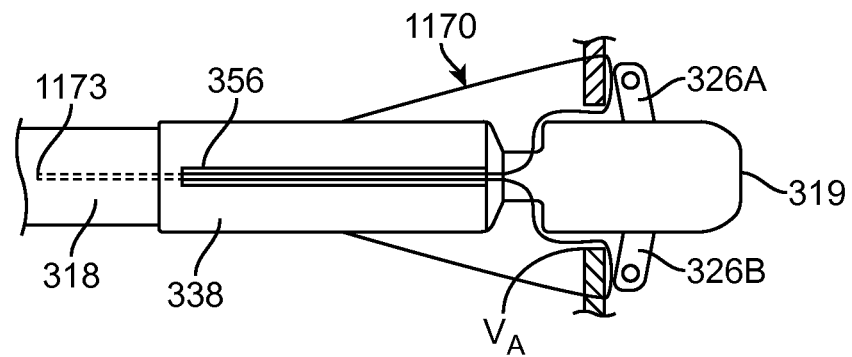

Once suture mounting portions 329A, 329B and first and second ends 1172, 1174 of suture 1170 coupled thereto are effectively captured by needles 330A, 330B, respectively, needles 330A, 330B are proximally retracted as shown in FIG. 12D. The needles and captured suture mounting portions and suture ends are proximally retracted until they are positioned within elongate body 318, as shown in FIG. 12E and described above. At this point in the method of operation, suture 1170 exits from proximal suture guide 356 of needle guide 338 and follows the path taken by needles 330A, 330B.

The captured ends of the suture are thus pulled through tissue on opposing sides of the incision/arteriotomy via the pathways/incisions created by needles 330A, 330B. Since the ends of the suture are being proximally retracted by needles 330A, 330B, intermediate portion 1173 of suture 1170 is pulled forward or distally advanced and approaches a proximal end of proximal suture guide 356 of needle guide 338 as shown in phantom in FIG. 12E.

Figure 12F:
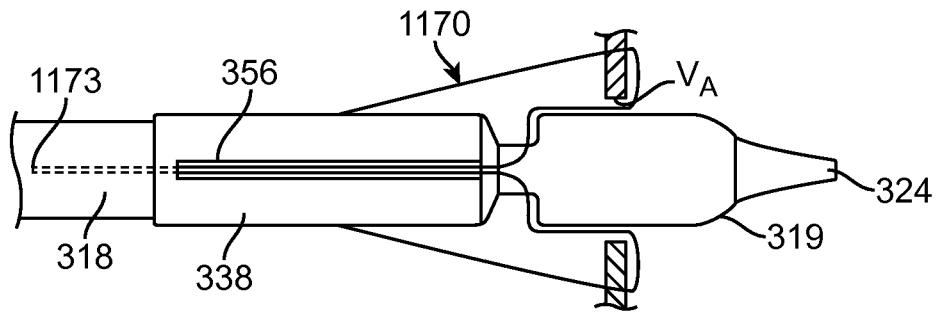
Figure 12G:
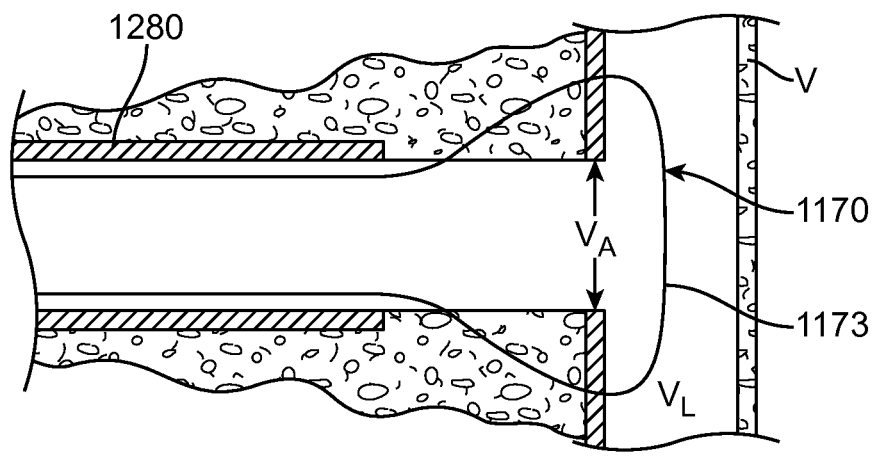

Distal tip 324 is extended to collapse support arms 326A, 326B, as shown in FIG. 12F via distal advancement of the inner shaft as described above with respect to inner shaft 334. Suturing device 320 may then be retracted and removed. As suturing device 320 is retracted, intermediate portion 1173 of suture 1170 is pulled forward or distally advanced and exits from proximal suture guide 356 of needle guide 338, thereby releasing intermediate portion 1173 of suture 1170 into the vessel lumen of the vessel having an incision/arteriotomy. More particularly, as shown in FIG. 12G, suture 1170 is shown positioned in a vessel V having a lumen $V_L$ and an incision/arteriotomy $V_A$ after suturing device 320 is removed. Intermediate portion 1173 extends within lumen $V_L$ of vessel V adjacent to incision/arteriotomy $V_A$. Suture 1170 extends through the vessel wall on opposing sides of the incision/arteriotomy, and proximally extends back to suturing device 320 with ends 1172, 1174 (not shown in FIG. 12G) still captured by needles 330A, 330B, respectively.

After the suturing device 320 is withdrawn, suture 1170 remains in situ with the intermediate portion 1173 extending within lumen $V_L$ of vessel V adjacent to incision/arteriotomy $V_A$ and the remaining length of suture 1170 extends through an introducer sheath 1280 which remains in situ throughout the suturing method in order to provide access to incision/arteriotomy $V_A$. In another embodiment hereof, since suturing device 320 includes a retractable distal tip that does not interfere with the opposing side of the vessel wall, suturing device 320 may be delivered to incision/arteriotomy $V_A$ without an introducer sheath. The physician pulls on or applies tension to suture ends 1172, 1174 to close the incision/arteriotomy $V_A$. The physician then ties or forms at least one surgical knot with the ends of suture 1170 and slides or pushes the knot(s) down along the length of the suture. Alternatively, the physician may fasten a small, circular or flat stainless steel clip (not shown) to the ends of the suture 1170 and slide or push the clip down along the length of the suture until it is adjacent to incision/arteriotomy $V_A$. A trimmer may be utilized to cut and remove the extra length of suture 1170, and introducer sheath 1280 may be removed from the patient.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A suturing device, comprising:
    an elongated body;
    a distal tip that is moveable between an extended position in which the distal tip distally extends from a distal end of the elongated body and a retracted position in which the distal tip is disposed within the elongated body;
    at least two support arms pivotally coupled to the distal tip to be actuated by longitudinal movement of the distal tip, wherein each support arm is in a collapsed position disposed within the elongated body when the distal tip is in the extended position and each support arm is in a deployed position extending radially away from the elongated body when the distal tip is in the retracted position; and
    at least two needles being extendable and retractable relative to the elongated body, wherein each needle includes a distal end configured to penetrate through a vessel wall and capture a suture releasably held within a portion of a support arm.

2. The suturing device of claim 1, wherein a proximal end of the distal tip is coupled to an inner shaft that is movable within a lumen of the elongated body.

3. The suturing device of claim 2, wherein a surface of each support arm wedges between the elongated body and an outer surface of the distal tip to lock each support arm in the deployed position.

4. The suturing device of claim 1, wherein each support arm includes a suture mounting portion having an opening sized to receive the distal end of the needle and to engage the needle by interference fit.

5. The suturing device of claim 4, wherein the opening of the suture mounting portion is D-shaped and the suture mounting portion is injection molded into the recess of the support arm.

6. The suturing device of claim 1, wherein the at least two support arms includes first and second support arms that are circumferentially spaced approximately 180 degrees from each other.

7. The suturing device of claim 1, wherein the at least two support arms includes first, second, third, and fourth support arms that are circumferentially spaced approximately 90 degrees from each other.

8. The suturing device of claim 1, wherein the elongated body comprises:
    an outer shaft;
    a needle guide coupled to a distal end of the outer shaft; and
    an end cap coupled to a distal end of the needle guide.

9. The suturing device of claim 8, wherein a proximal end of the needle guide is threaded into a distal end of an elongated tabular shaft and a distal end of the needle guide is threaded onto a proximal end of an end cap.

10. The suturing device of claim 8, wherein the needle guide includes
    at least two profiled passageways for guiding the at least two support arms between the collapsed position in which the support arm is disposed within the elongated body and the deployed position in which the support arm extends radially away from the elongated body and
    at least two transverse ports for guiding the at least two needles between a retracted position in which the needle is disposed within the body and an extended position in which the needle extends distally and outwardly from the elongated body, the transverse ports each including a first segment having a first width and a second segment having a second width greater than the first width.

11. The suturing device of claim 10, wherein the at least two needles are formed from stainless steel.

12. The suturing device of claim 10, wherein the needle guide is a single component.

13. The suturing device of claim 10, wherein the needle guide also includes an intermediate necked portion having a reduced outer diameter, a proximal suture guide slot proximally extending from a proximal end of the intermediate necked portion of the needle guide, and at least two distal suture guide slots distally extending from a distal end of the intermediate necked portion to the at least two profiled passageways for guiding the at least two support arms.

14. The suture device of claim 13, further comprising:
a suture at least partially disposed within the elongated body when the support arms are in the collapsed position, wherein a first end of the suture is coupled to a first support arm and a second end of the suture is coupled to a second support arm, and the suture extends from within the at least two profiled passageways, through the two distal suture guide slots, alongside the intermediate necked portion of the needle guide, through the proximal suture guide slot, and within the needle guide.

15. A suturing device for positioning a suture in situ, comprising:
an elongated body defining at least one lumen there through;
an inner shaft slidably extending within the at least one lumen of the elongated body;
a distal tip coupled to a distal end of the inner shaft, the distal tip being moveable between an extended position in which the distal tip distally extends from a distal end of the elongated body and a retracted position in which the distal tip is disposed within the elongated body;
at least two support arms pivotally coupled to the distal tip such that deployment of the support arms is actuated by movement of the distal tip, wherein each support arm is in a collapsed position disposed within the elongated body when the distal tip is in the extended position and each support arm is in a deployed position extending radially away from the elongated body when the distal tip is in the retracted position; and
at least two needles being extendable and retractable relative to the elongated body, wherein each needle includes a distal end configured to penetrate through a vessel wall and capture a suture releasably held within a portion of a support arm.

16. The suturing device of claim 15, wherein the elongated body comprises:
an outer shaft;
a needle guide coupled to a distal end of the outer shaft; and
an end cap coupled to a distal end of the needle guide,
the needle guide including an intermediate necked portion having a reduced outer diameter, a proximal suture guide slot proximally extending from a proximal end of the intermediate necked portion of the needle guide, and at least two distal suture guide slots distally extending from a distal end of the intermediate necked portion to at least two profiled passageways for guiding the at least two support arms.

17. The suture device of claim 16, further comprising:
a suture disposed within the elongated body when the support arms are in the collapsed position, wherein a first end of the suture is coupled to a first support arm and a second end of the suture is coupled to a second support arm, and the suture extends from within the at least two profiled passageways, through the two distal suture guide slots, alongside the intermediate necked portion of the needle guide, through the proximal suture guide slot, and within the needle guide.

18. The suturing device of claim 17, wherein the first and second ends of the suture are coupled to the first and second support arms via first and second suture mounting portions that are disposed on each respective support arm.

19. The suturing device of claim 18, wherein the suture mounting portions each have an opening sized to receive the distal end of the needle and to engage the needle by interference fit.

20. The suturing device of claim 19, wherein the openings of the suture mounting portions are D-shaped and the suture mounting portions are injection molded into the recesses of the support arms.

* * * * *